United States Patent [19]

Schuelke et al.

[11] Patent Number: 5,755,742
[45] Date of Patent: May 26, 1998

[54] CARDIOVERSION/DEFIBRILLATION LEAD IMPEDANCE MEASUREMENT SYSTEM

[75] Inventors: Robert J. Schuelke, Lakeville; Barbara J. Schmid, Minneapolis; Jonathan R. Gering, St. Louis Park, all of Minn.

[73] Assignee: Medtronic, Inc., Minneapolis, Minn.

[21] Appl. No.: 741,757

[22] Filed: Nov. 5, 1996

[51] Int. Cl.⁶ .................................................. A61N 1/37
[52] U.S. Cl. .............................. 607/27; 607/8; 128/734
[58] Field of Search ............................. 607/4, 5, 8, 9, 607/27, 28; 128/734

[56] References Cited

U.S. PATENT DOCUMENTS

| | | | |
|---|---|---|---|
| 4,727,877 | 3/1988 | Kallok. | |
| 4,899,750 | 2/1990 | Ekwall. | |
| 5,003,975 | 4/1991 | Hafelfinger et al.. | |
| 5,117,824 | 6/1992 | Keimel et al.. | |
| 5,163,427 | 11/1992 | Keimel. | |
| 5,215,081 | 6/1993 | Ostroff | 607/8 |
| 5,312,441 | 5/1994 | Mader et al. | 607/5 |
| 5,431,692 | 7/1995 | Hansen et al. | 607/28 |
| 5,534,018 | 7/1996 | Wahlstrand et al. | 607/27 |
| 5,549,646 | 8/1996 | Katz et al. | 607/8 |

FOREIGN PATENT DOCUMENTS

WO 92/18198   10/1992   WIPO.

OTHER PUBLICATIONS

Olson et al., "Onset and Stability for Ventricular Tachyarrhythmia Detection in an Implantable Pacer-Cardioverter-Defibrillator" *Computers in Cardiology*, Oct. 7–10, 1986, IEEE Computer Society Press, pp. 167–170.

Arzbaecher et al., "Automatic Tachycardia Recognition", *PACE*, vol. 7, May–Jun. 1984, part II, pp. 541–547.

Mead et al., "Evaluation and Potential Application of a New Method for Measuring Pacing Lead Impedance", *PACE*, vol. 18, No. 2, p. 817, Apr. 1995, Part II.

*Primary Examiner*—Jeffrey R. Jastrzab
*Attorney, Agent, or Firm*—Reed A. Duthler; Harold R. Patton

[57] ABSTRACT

A lead integrity measurement system for a cardiac pacemaker/cardioverter/defibrillator (PCD) of the type comprising an implantable pulse generator (IPG) and a lead system including one or more pacing leads each having a proximal end coupled to a pacing terminal of the IPG and a distal end with at least one pace/sense electrode in contact with a patient's heart and a pair of defibrillation leads coupled to defibrillation terminals of the IPG and defibrillation electrodes implanted in relation to the patient's heart. In a lead impedance test mode, the terminal of a selected defibrillation lead under test is coupled to system ground, and an excitation voltage is applied in an excitation path from a force lead terminal selected from the pacing leads. A measure lead is selected from among the other of the pacing leads and defibrillation leads, and the voltage induced in the lead under test is measured through the measure lead and the electrode/tissue interface of the measure lead and the defibrillation lead under test. The applied current in the excitation path is also measured, and an impedance value is derived from the measured current and voltage values. The test is continued with other selections of excitation and measure paths. Comparisons of the measured impedances with maximum and minimum impedance values are used to determine lead integrity failures. The lead impedance between two defibrillation leads is determined as a function of the sum of the derived defibrillation lead impedances.

20 Claims, 5 Drawing Sheets

CARDIOVERSION/DEFIBRILLATION LEAD IMPEDANCE MEASUREMENT SYSTEM

CROSS-REFERENCE TO RELATED APPLICATIONS

Reference is hereby made to commonly assigned, U.S. patent application Ser. No. 08/346,661 filed Nov. 30, 1994 now U.S. Pat. No. 5,534,018 in the names of J. D. Wahlstrand et al. for AUTOMATIC LEAD RECOGNITION FOR IMPLANTABLE MEDICAL DEVICE.

FIELD OF THE INVENTION

The present invention generally relates to implantable pacemaker/cardioverter defibrillators and more particularly to a method and apparatus for measuring lead impedance and determining lead integrity employing sub-threshold excitation pulses.

BACKGROUND OF THE INVENTION

By way of definition, in the field of automatic implantable arrhythmia control devices, e.g. implantable cardioverter/defibrillators (ICDs) and pacemaker/cardioverter/defibrillators (PCDs) the term "cardioversion" or "cardioverter" refers to the process of and device for discharging relatively high energy electrical shocks into or across cardiac tissue to arrest a life threatening tachyarrhythmia. The delivery of cardioversion shocks may or may not be synchronized with a cardiac depolarization or rhythm and may be applied to arrest a malignant ventricular tachycardia or ventricular fibrillation with a selectable or programmable shock energy. In practice, the arrest of atrial or ventricular tachycardia or fibrillation by such shocks delivered in synchrony with a cardiac depolarization is typically referred to as "cardioversion". Similarly, the arrest of atrial or ventricular fibrillation by a shock delivered without such synchronization is typically referred to as "defibrillation". In the following description and claims, it is to be assumed that these terms are interchangeable, and that use of one term is inclusive of the other device or operation, unless specific distinctions are drawn between them.

Current implantable pulse generator (IPG) and associated lead systems for the treatment of tachyarrhythmias, e.g. the MEDTRONIC Model 7217 PCD device and associated leads, provide sensing of tachyarrhythmias and programmable staged therapies including anti-tachycardia pacing regimens and cardioversion energy and defibrillation energy shock regimens in order to terminate the sensed tachyarrhythmia with the most energy efficient and least traumatic therapies (if possible). The Model 7217 PCD IPG provides a programmable energy, single polarity wave form, shock from the discharge of a high voltage output capacitor bank through a pair of electrodes disposed in relation to the heart. The Model 7217 PCD IPG also provides programmable single chamber bradycardia pacing therapies through pace/sense electrodes.

In recent years, dual chamber cardiac pacemakers have also been suggested for incorporation into PCDs, as exemplified by commonly assigned U.S. Pat. No. 5,312,441, for example. Such PCDs provide programmable staged therapies including anti-tachycardia pacing regimens and cardioversion energy and defibrillation energy shock regimens in order to terminate a tachyarrhythmia with the most energy efficient and least traumatic therapies (if possible), as well as single or dual chamber, DDD, bradycardia pacing therapies. In such dual chamber PCDs, the atrial and ventricular pacing pulse generators, sense amplifiers and associated timing operations are incorporated into the system with atrial and ventricular pace/sense leads and electrodes. Various pacing modes may be programmed for recognizing and providing bradycardia and tachycardia pacing Typically, unipolar or bipolar pace/sense leads bearing pace/sense electrodes and associated lead conductors and connector elements are either incorporated into a single pacing lead body or into a combined pacing and defibrillation lead body also bearing one or more defibrillation electrodes and associated defibrillation lead conductor(s) and connector element(s). A wide variety of pacing and defibrillation leads have been proposed for positioning endocardially within a heart chamber or associated blood vessel or epicardially about the heart chambers or more remotely in subcutaneous locations. At least two such electrodes are required to define a current pathway encompassing a heart chamber to be paced or defibrillated. In unipolar pacing, the IPG case is typically employed as one pace/sense electrode for a pacing pathway. In ICD and PCD lead systems, the IPG case or a subcutaneous patch electrode may be employed as one defibrillation electrode. In certain ICD and PCD systems, the IPG case or subcutaneous electrode is electrically connected in common with an epicardial of endocardial defibrillation electrode. A wide variety of combinations of defibrillation electrodes located inside or outside the right atrium (RA), extending into or over the superior vena cava (SVC) in many cases, inside or outside the right ventricle (RV) inserted into the great vein and coronary sinus (CS) and exteriorly across the atria and ventricles have been proposed.

For convenience, in the following description and claims, a "pacing lead" is defined as a pace/sense electrode (including the case where the pacing lead is only used for pacing or for sensing), a proximal end pacing lead connector element for attachment to a terminal of a PCD IPG, and a pacing lead conductor within a lead body electrically connecting the pace/sense electrode and the pacing lead connector element. The "lead impedance" of such a pacing lead is also defined as including the impedance of these components of the pacing lead as well as any impedance of the connection of the connector element with the IPG terminal. Similarly, a "defibrillation lead" is defined as a defibrillation electrode, a proximal end defibrillation lead connector element for attachment to a terminal of a PCD IPG, and a defibrillation lead conductor within a lead body electrically connecting the defibrillation electrode and the defibrillation lead connector element. The "lead impedance" of such a defibrillation lead is also defined as including the impedance of these components of the defibrillation lead as well as any impedance of the connection of the connector element with the IPG terminal. These definitions encompass any combination of two or more pacing leads or defibrillation leads incorporated into the same lead body and any combinations of pacing lead(s) and defibrillation lead(s) in the same lead body. The "lead impedance" in the special case of the exposed IPG can as a pace/sense electrode or a defibrillation electrode includes any connection elements for connecting the IPG can to sensing circuitry or to pacing pulse or defibrillation shock output circuit(s).

In such PCD systems, the integrity of the pace/sense leads and/or defibrillation leads, and the integrity of the connections of the proximal lead connector elements with IPG terminals, is of great importance. Lead insulation failures, interior lead conductor wire fracture or fractures with other lead parts, and loose, intermittent connections with the IPG connector terminals can occur. When lead integrity is compromised, the lead impedance may increase or decrease affecting the sensing of cardiac signals and the delivery of adequate energy to the heart during cardioversion/defibrillation and/or pacing therapies.

The above-referenced '661 application describes a system for automatically recognizing the type of lead (i.e., unipolar or bipolar) attached to a dual chamber pacemaker when the leads are attached to the IPG connector terminals and also for automatically periodically testing bipolar lead integrity. Lead integrity failures are detected by entering a test routine and directly injecting a sub-threshold voltage pulse into a pair of lead connector terminals and measuring current flow during delivery of the voltage pulse. The lead impedance is determined as a simple function of the voltage divided by the current. A high variance from impedance range specifications of the lead provide an indication of either a fracture in the lead body or a connection failure with the IPG connector terminal. A low impedance variance from the lead impedance range specifications is indicative of a short. With respect to bipolar pacing leads, each lead conductor and associated electrode is tested in the same manner.

In cardiac pacemaker IPGs, the lead integrity check may also be undertaken during delivery of a pacing pulse. Pacing pulses are not perceptible, and therefore the patient is not aware that the testing is taking place. Consequently, such testing may be undertaken at regular intervals, and the collected lead impedance data can be stored within IPG memory for transmission out to an external programmer through uplink telemetry on receipt of an interrogation command from the programmer. A pacing lead or electrode failure may be a gradual process, and the collected lead impedance data may signify an impedance trend suggesting an impending failure that may be monitored more closely or may result in replacement of the lead or re-positioning of the lead electrode.

The integrity of the defibrillation leads and electrodes is of utmost importance, since the inability to conduct sufficient cardioversion/defibrillation shock energy to a heart chamber in fibrillation may result in failure to defibrillate and possible death. The impedance testing of the defibrillation lead or electrode in the manner described above for a pacing lead system would require the addition of bulky and current consuming protection circuitry within the IPG proximal to the defibrillation terminals. In PCD systems, the delivered defibrillation shocks induce currents and voltages in the pace/sense electrodes and leads that are conducted through the IPG pace/sense lead connector terminals and, if high voltage protection were not provided, would cause damage to the sense amplifiers and pacing pulse generators coupled thereto. If circuitry for directly injecting a low energy test pulse across defibrillation leads and electrodes is provided, it must be protected from the high voltage cardioversion/defibrillation shock energy by use of bulky and expensive semiconductor switches which may themselves be a source of potential failure during delivery of cardioversion/defibrillation therapies.

Moreover, in endocardial pacing leads, unipolar and bipolar lead configurations are the norm, whereas tripolar endocardial lead configurations are coming into use in PCD systems. Such tripolar endocardial leads typically include a distal tip and proximal ring, pace/sense electrode pair and an elongated, proximally extending, defibrillation electrode for either atrial or ventricular placement and three lead conductors connecting the electrodes with proximal connector elements. Such a tripolar ventricular lead is shown, for example, in the above-referenced '441 patent where the coiled wire, lead conductors, electrodes and terminal elements for each such electrode are separated from one another by insulating sheaths and/or coatings. Other tripolar leads are proposed employing "straight" conductor wires arranged to extend in parallel with one another. In either case, it is desirable to test such tripolar lead insulation and lead conductor integrity as a lead system because electrical short circuits between adjacent lead conductors or electrical open circuits in the connections of one of the lead conductors with the associated proximal lead connector element or the distal electrode may be mis-diagnosed when tests are conducted in the manner set forth in the '661 patent application. When a lead integrity failure is indicated by the impedance measurement, it is not always clear where the failure resides.

Accordingly, a need exists for a simple system for measuring defibrillation lead impedance from which lead integrity can be ascertained accurately that is not wasteful of energy and painful to the patient and does not require bulky protection circuitry for protecting the impedance measuring circuitry from cardioversion/defibrillation shock energy.

SUMMARY OF THE INVENTION

It is therefore an object of the present invention to provide a practical and reliable system in an implantable tissue stimulator, particularly a PCD IPG and associated lead system for measuring the impedance of leads, particularly defibrillation leads without adding cost and bulk to the system.

It is a further object of the present invention to provide such a PCD IPG having a lead impedance measurement feature for measuring the impedance of defibrillation leads using low energy force pulses that are imperceptible to the patient.

It is a still further object of the present invention to provide such a PCD IPG having an automatic lead impedance measurement feature for measuring the impedance of defibrillation leads and pacing leads on a regular basis and for storing lead impedance data that may be telemetered out to an external programmer for analysis of potential lead integrity failures.

These and other objects of the invention are realized in a tissue stimulation system having a pulse generator coupled through at least three terminals to at least three leads each having an electrode in contact with body tissue at an electrode/tissue interface, a system and method for testing current and voltage lead integrity of at least one of the leads comprising the steps of and means for: selecting one of the at least three leads as a lead under test, a force lead and a measure lead; coupling the terminal of the lead under test to a fixed potential; driving an excitation voltage pulse in an excitation path including the terminal of the selected force lead, the force lead electrode/tissue interface, the lead under test electrode/tissue interface and the lead under test; measuring the excitation current value of the excitation voltage pulse delivered in the excitation path through the lead under test; and measuring an induced voltage in a measure path including the terminal of the selected measure lead, the measure lead electrode/tissue interface, the lead under test electrode/tissue interface and the lead under test. The lead impedance of the lead under test is derived from the measured excitation current value and the induced voltage value. In order to test the lead integrity of the remaining leads, the selection of the lead under test, the force lead and the measure lead are changed, and the test is repeated.

Preferably, the system and method of the invention is implemented in a PCD IPG and associated defibrillation lead system having at least first and second defibrillation leads each having defibrillation electrodes positionable in relation to a patient's heart for providing a defibrillation shock pathway through the patient's heart and an associated pacing lead system having first and second pace/sense electrodes positioned in relation to a patient's heart for providing a pace/sense pathway through the patient's heart and electrically connected to the PCD IPG and comprises the means for and steps of: applying a force pulse of known voltage having insufficient energy to capture the heart into a first excitation pathway including the first pacing lead, the patient's body tissue and the first defibrillation lead; measuring the current in the first excitation pathway during the force pulse; measuring an induced voltage, induced in response to the force pulse, across a first measure pathway including one of the second defibrillation lead or the second pacing lead, the patient's heart, and the first defibrillation lead; and deriving the impedance of the first defibrillation lead in response to the known voltage of the first force pulse, the measured current in the first excitation pathway, and the measured voltage of the induced voltage.

In order to derive the impedance of the second defibrillation lead, the steps are repeated with substitution of the second defibrillation lead for the first defibrillation lead. Additional defibrillation lead impedances may be derived in the same manner by use of any combination of the defibrillation lead under test and two other pacing or defibrillation leads.

The present invention provides the PCD IPG with the ability to periodically enter the lead impedance test mode, derive defibrillation lead impedances and store the impedance measurements for later retrieval and analysis by the physician. Preferably, lead impedances are also compared to upper and lower threshold levels, and an alarm perceptible to the patient may be generated if the lead impedance falls outside the range defined by the upper and lower limits.

The defibrillation lead impedances may be conducted with sub-threshold lead impedance test pulses that are not perceived by the patient and that are energy efficient and do not contribute to premature battery depletion. Moreover, due to the use of a pacing lead and the patient's body tissue for injecting the lead impedance test pulses and for measuring the injected currents and induced voltages, direct connection of pulse generators and sensing amplifiers with the defibrillation leads under test is avoided, and bulky and expensive protection circuits are not required.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

The preferred embodiments of the invention are preferably implemented in the context of an implantable PCD having single or dual chamber pacing and/or cardioversion/ defibrillation capabilities of the types described in detail in the above-referenced '441 patent and in commonly assigned, U.S. patent application Ser. No. 08/293,769 filed Aug. 19, 1994, now U.S. Pat. No. 5,549,642 for ATRIAL DEFIBRILLATOR AND METHOD OF USE, respectively, incorporated herein by reference in their entireties.

Figure 1:
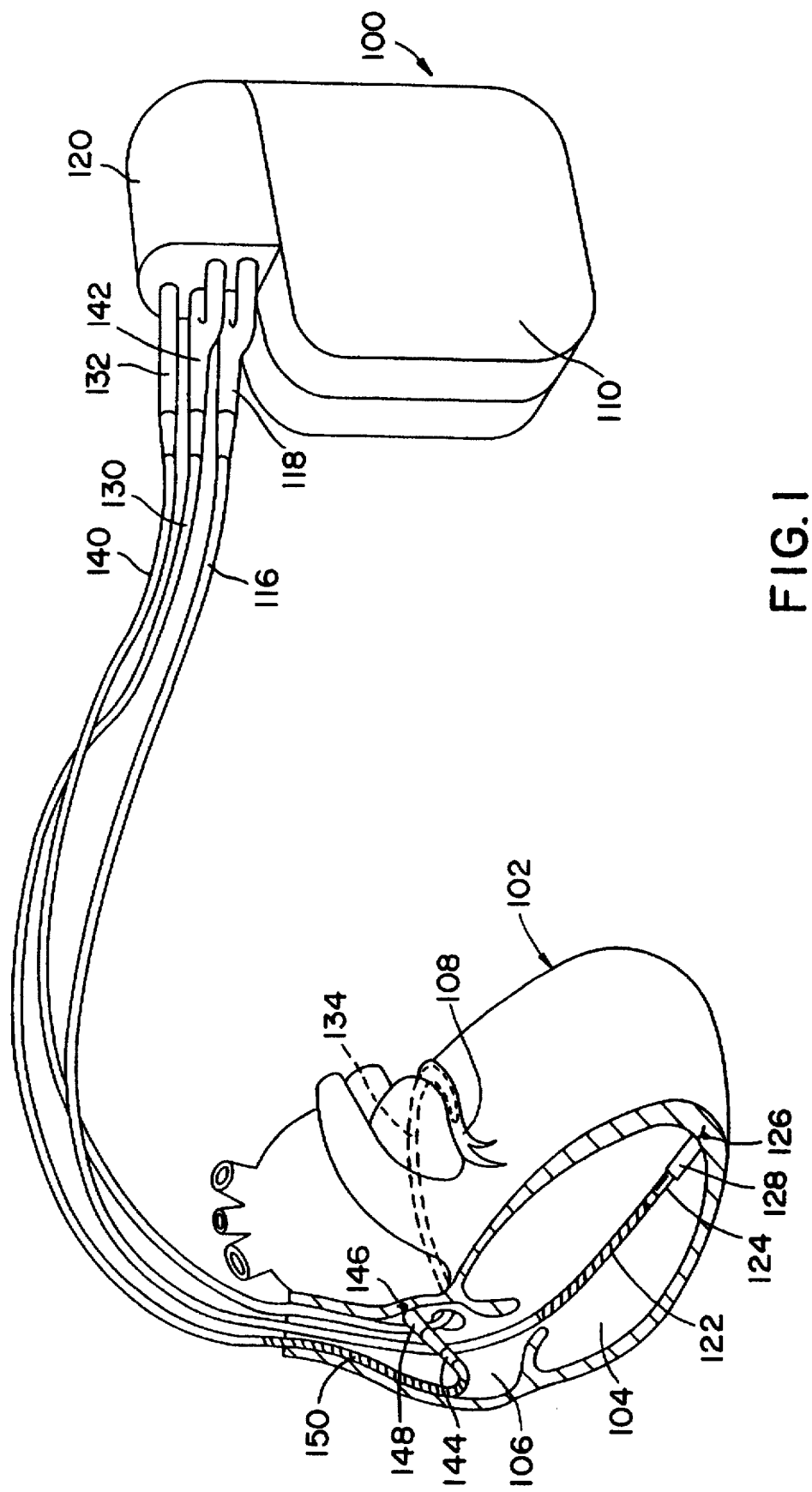
FIG. 1 is a schematic illustration of an atrial and ventricular chamber pacemaker/cardioverter/defibrillator IPG implanted in a patient's chest with am IPG CAN electrode and endocardial leads transvenously introduced into the RA, CS and RV of the heart wherein current and voltage measurements across selected pace/sense and cardioversion/ defibrillation electrode pairs may be made.
Figure 2:
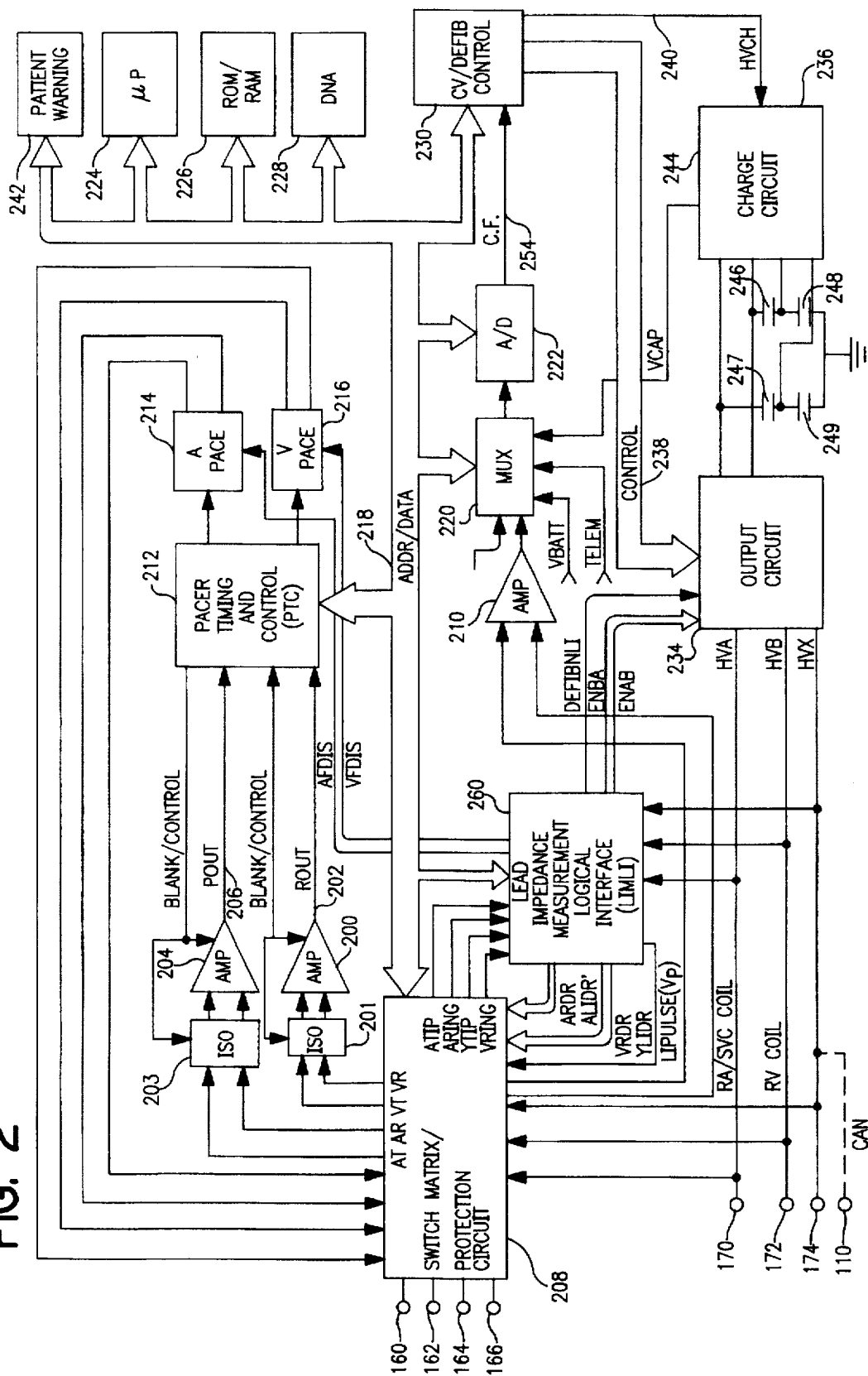
FIG. 2 is a simplified block diagram of the IPG of FIG. 1 in which the present invention may be practiced by applying force pulses through delivery lead terminal pairs and monitoring the delivered current and evoked voltage response across measure terminal pairs.

FIGS. 1 and 2 illustrate such a dual chamber, multi-programmable, PCD IPG and associated lead system for providing atrial and/or ventricular sensing functions for detecting P-waves of atrial depolarizations and/or R-waves of ventricular depolarizations, depending on the programmed operating mode, determining bradycardia and tachycardia, and delivering programmed therapy regimens for each. FIGS. 1 and 2 are intended to provide a comprehensive illustration of different atrial and ventricular, pacing and cardioversion/defibrillation configurations that may be effected using combinations of the components thereof. For example, in the specific embodiment of FIGS. 5–7, only a single cardioversion/defibrillation pathway is depicted and described. Such PCDs may be constructed or made programmable to provide atrial only, ventricular only, or both atrial and ventricular pacing modes. The pacing modes also preferably include either or both bradycardia compensating pacing modes or anti-tachycardia pacing therapies. The present invention may be employed with a wide variety of cardioversion/defibrillation lead and electrode combinations.

In accordance with the invention, FIGS. 1 and 2 also show in a simplified manner, a system for conducting the lead integrity test for use with pace and cardioversion/ defibrillation leads, including combinations thereof, and without providing special protective circuitry in the cardioversion/defibrillation high voltage pathway. First, the general configuration of the comprehensive dual chamber PCD system will be described.

In the preferred embodiment of FIGS. 1 and 2, depending on the programmed pacing mode, pacing pulses may be applied to the atrium and/or ventricle in response to the detection of the appropriate bradycardia condition by the PCD IPG 100. The pacing and sensing functions are effected through atrial and ventricular, bipolar tip and ring, pace/ sense electrode pairs at the ends of right atrial/superior vena cava (RA) and right ventricular (RV) leads 140 and 116, respectively, fixed in the right atrium 106 and right ventricle 104, respectively, that are electrically coupled to the circuitry of IPG 100 through a connector block 120. Delivery of cardioversion or defibrillation shocks to the atrial and/or ventricular chambers of the heart 102 may be effected through selected combinations of the illustrated exemplary RA and RV cardioversion/defibrillation electrodes on the RA and RV leads and an additional coronary sinus (CS) electrode 134 on a CS lead 130 as well as an exposed surface of the outer housing or can of the IPG 100. The exposed case or "CAN" electrode 110 optionally serves as a subcutaneous cardioversion/defibrillation electrode, used as one electrode optionally in combination with one intracardiac cardioversion/defibrillation electrode for cardioverting or defibrillating either the atria or ventricles. A subcutaneous cardioversion/defibrillation electrode may be provided in addition to or substitution for the CAN electrode 110.

The RV lead 116 is depicted in a conventional configuration and includes an elongated insulated lead body, enclosing three concentric, electrically isolated, coiled wire conductors, separated from one another by tubular insulated sheaths. Located adjacent the distal end of the RV lead 116 are a pace/sense ring electrode 124, a helical, pace/sense electrode 126, mounted retractably within an insulated electrode head 128. Helical tip electrode 126 is adapted to be extended out of the electrode head 128 and screwed into the ventricular apex in a manner well known in the art. RV pace/sense electrodes 124 and 126 are each coupled to a coiled wire conductor within the RA lead body and are employed for cardiac pacing in the ventricle and for sensing near-field R-waves. RV lead 116 also supports an elongated, exposed wire coil, cardioversion/defibrillation electrode 122 (hereafter "RV COIL" electrode) a distal segment thereof adapted to be placed in the right ventricle 104 of heart 102. RV COIL electrode 122 may be fabricated from platinum, platinum alloy or other materials known to be usable in implantable cardioversion/defibrillation electrodes and may be about 5 cm in length. RV COIL electrode 122 is also coupled to one of the coiled wire conductors within the lead body of RV lead 116. At the proximal end of the lead body is a bifurcated connector end 118 having three exposed electrical connectors, each coupled to one of the coiled conductors, that are attached within the connector block 120 to connector block terminals in a manner well known in the art.

The coronary sinus (CS) lead 130 includes an elongated insulated lead body enclosing one elongated coiled wire conductor coupled to an elongated exposed coil wire cardioversion/defibrillation electrode 134. Electrode 134, illustrated in broken outline, is located within the coronary sinus and great vein 108 of the heart 100 and may be about 5 cm in length. At the proximal end of the CS lead 130 is a connector end 132 having an exposed connector coupled to the coiled wire conductor and attached within the connector block 120 to connector block terminals in a manner well known in the art.

The RA lead 140 includes an elongated lead body carrying three concentric, electrically isolated, coiled wire conductors separated from one another by tubular insulated sheaths, corresponding generally to the structure of the RV lead 116. The lead body is formed in a manner well known in the art in an atrial J-shape in order to position its distal end in the right atrial appendage. A pace/sense ring electrode 144 and an extendable helical, pace/sense electrode 146, mounted retractably within an insulated electrode head 148, are formed distally to the bend of the J-shape. Helical tip electrode 146 is adapted to be extended out of the electrode head 148 and screwed into the atrial appendage in a manner well known in the art. RA pace/sense electrodes 144 and 146 are employed for atrial pacing and for near-field sensing of P-waves. An elongated, exposed cardioversion/defibrillation RA/SVC COIL electrode 150 is supported on RA lead 140 extending proximally to pace/sense ring electrode 144 and coupled to the third coiled wire conductor within the RA lead body. RA/SVC COIL electrode 150 preferably is 10 cm in length or greater and is configured to extend from within the SVC and toward the tricuspid valve. At the proximal end of the RA lead 15 is a bifurcated connector 13 which carries three exposed electrical connectors, each coupled to one of the coiled wire conductors, that are attached within the connector block 120 to connector block terminals in a manner well known in the art.

The circuitry within IPG 100 communicates with an external programmer (not shown) through an RF communication link in a manner well known in the art. The lead integrity test may be initiated by commands from the external programmer in a manner well known in the art, to select lead conductor pairs and collect impedance data for analysis as described in detail below. In addition, in accordance with the present invention, the circuitry may initiate a lead integrity test sequence automatically on a periodic basis, e.g. when the patient is expected to be sleeping, to obtain such lead data for transmission out of the IPG 100 upon interrogation at a later time.

The PCD system configuration and operating modes of FIG. 1 may be varied by eliminating: (1) the atrial or ventricular pacing capability including the associated pace/sense electrodes thereby providing dual chamber cardioversion/defibrillation and single chamber bradycardia/tachycardia pacing capabilities; (2) in a single chamber PCD, the atrial or ventricular pacing and sensing capability along with the corresponding chamber cardioversion/defibrillation capability and associated leads and electrodes; (3) single chamber, atrial or ventricular, cardioversion/defibrillation capability and associated leads/electrodes while retaining the dual chamber pacing and sensing capability thereby providing single chamber cardioversion/defibrillation and dual chamber bradycardia/tachycardia pacing capabilities; or (4) in a special case of an atrial PCD, the ventricular cardioversion/defibrillation capability while retaining at least the atrial pace/sense capability and the ventricular sense capability for providing R-wave synchronization of the delivered atrial cardioversion therapies. The present invention is independent of the configuration but is of particular use in a configuration using at least one tripolar endocardial lead system.

FIG. 2 is a functional schematic diagram of the circuitry of a comprehensive dual chamber, implantable pacemaker/cardioverter/defibrillator 100 in which the present invention may usefully be practiced. Certain of the pace/sense and cardioversion/defibrillation functions may be disabled or not provided to configure the PCD device to operate in other dual chamber or single chamber PCD operating modes including the above-described modes (1)–(4). Therefore, FIG. 2 should be taken as exemplary of the circuitry of the type of PCD IPG 100 in which the invention may be embodied, and not as limiting, as it is believed that the invention may usefully be practiced in a wide variety of device implementations, as long as a pacing mode providing either bradycardia pacing or tachycardia pacing therapies is retained.

The PCD IPG circuitry of FIG. 2 includes a high voltage section for providing relatively high voltage cardioversion/ defibrillation shocks when needed in response to detection of a tachyarrhythmia, a low voltage pace/sense section for sensing P-waves and/or R-waves and providing relatively low voltage bradycardia pacing and anti-tachycardia pacing therapies, both operated under the control of a microcomputer including a microprocessor 224, ROM/RAM 226 and DMA 228. Other functions, including uplink and downlink telemetry with an external programmer for interrogating or programming operating modes and parameters, are also provided in a manner well known in the art.

The block diagram of FIG. 2 depicts the atrial and ventricular pace/sense and cardioversion/defibrillation lead connector terminals of the connector block 120. Assuming the electrode configuration of FIG. 1, the correspondence to the illustrated leads and electrodes is as follows: Optional CAN electrode 110 can be hard wired or programmably substituted for the defibrillation electrode terminal 174. Otherwise, terminal 174 may be used and coupled to the CV lead connector 132 and to CV electrode 134 or to a subcutaneous patch electrode. Terminal 172 is adapted to be coupled through RV lead 116 to RV COIL electrode 122. Terminal 170 is adapted to be coupled through RA lead 140 to RA/SVC COIL electrode 150. However, it will be understood that fewer terminals may be provided than depicted, and/or that one or more differing cardioversion/defibrillation leads, e.g. epicardial patch electrode and subcutaneous patch electrode bearing leads may also be employed for one or more of the depicted cardioversion/defibrillation electrode bearing leads.

Terminals 164 and 166 are adapted to be coupled through lead 116 to RV pace/sense electrodes 124 and 126 for sensing and pacing in the ventricle. Terminals 160 and 162 are adapted to be coupled through lead 140 to RA pace/sense electrodes 144 and 146 for sensing and pacing in the atrium. Preferably, bipolar pace/sense electrodes are employed in the practice of the invention, but their configuration, fixation in contact with and positioning with respect to the atria and ventricles may differ from those shown in FIG. 1.

Terminals 170, 172 and 174 or CAN electrode 110 are coupled to high voltage output circuit 234. High voltage output circuit 234 includes high voltage switches controlled by CV/DEFIB CONTROL logic 230 via control bus 238. The switches within circuit 234 control which electrodes are employed and which are coupled to the positive and negative terminals of the capacitor bank including a first capacitor pair 246 and 248 and a second capacitor pair 247 and 249 during delivery of the intermediate and high voltage cardioversion and defibrillation shocks. Preferably biphasic shocks are generated in "A" and "B" phases in a manner disclosed in the '441 patent and in commonly assigned U.S. Pat. No. 5,163,427 wherein an implantable cardioverter/defibrillator system which is capable of providing three defibrillation shock methods, with a minimum of control and switching circuitry, is disclosed. The output stage is provided with the two separate output capacitor banks 246, 248 and 247, 249 which are sequentially discharged during sequential shock defibrillation and simultaneously discharged during single or simultaneous shock defibrillation through a two or three defibrillation electrode system. Other cardioversion shock wave shapes have been proposed in conjunction with a variety of electrode systems in order to achieve more efficient cardioversion, including bi-phasic or multi-phasic wave form shocks generated in rapid sequence and applied to the same or separate electrode systems. Despite the additional complexity, it is expected that cardioversion may be achieved more rapidly after the onset of an arrhythmia and at lower current consumption. In order to achieve low current consumption, these stimulation therapy regimens require rapid and efficient charging of high voltage output capacitors 246–249 from low voltage battery power sources as well as efficient sequential (or simultaneous) discharge of the capacitors through the electrode systems employed.

Terminals 164 and 166 are coupled through switch matrix and protection circuit 208 to the R-wave sense amplifier 200 through an input isolation circuit 201. R-wave sense amplifier 200 preferably takes the form of an automatic gain controlled amplifier providing an adjustable sensing threshold as a function of the measured R-wave signal amplitude. A VSENSE signal is generated on R-OUT line 202 whenever the signal sensed between the VTIP and VRING electrodes appearing at terminals 164 and 166 exceeds the current ventricular sensing threshold. Terminals 160 and 162 are similarly coupled through switch matrix and protection circuit 208 through an input isolation circuit 203 to the P-wave sense amplifier 204, which preferably also takes the form of an automatic gain controlled amplifier providing an adjustable sensing threshold as a function of the measured P-wave amplitude. An ASENSE signal is generated on P-OUT line 206 whenever the signal sensed between ATIP, ARING electrodes coupled to terminals 160, 162 exceeds the current atrial sensing threshold. The APACE and VPACE output circuits 214 and 216 are also coupled (through certain components described below in reference to FIG. 5 and not shown in FIG. 2) to terminals 160, 162 and 164, 166, respectively. The atrial and ventricular sense amplifiers 204 and 206 are isolated from the APACE and VPACE output circuits 214 and 216 by appropriate isolation and blanking circuitry in each sense amplifier 204, 200 and the associated input isolation circuits 203, 201 operated by A-BLANK and V-BLANK signals during and for a short time following delivery of a pacing pulse in a manner well known in the art. The general operation of the R-wave and P-wave sense amplifiers 200 and 204 may correspond to that disclosed in U.S. Pat. No. 5,117,824, incorporated herein by reference in its entirety.

Switch matrix and protection circuit 208 is also used in an EGM sensing mode to select which of the available pace/sense electrodes are coupled to wide band (0.5–200 Hz) EGM sense amplifier 210 for use in digital signal storage and analysis of the patient's atrial and ventricular EGM. The selection of the terminals 160, 162 and 164, 166 is controlled by the microprocessor 224, via data/address bus 218, in order to apply atrial and ventricular signals to the bandpass amplifier 210. Alternatively, far field EGM signals may be measured by substituting the IPG CAN electrode 110 for one of the atrial and ventricular pace/sense electrodes coupled to the atrial and ventricular pace/sense terminals 160, 162 and 164, 166. In either case, output signals from bandpass amplifier 210 are provided to multiplexer 220, and thereafter converted to multi-bit digital signals by A/D converter 222, for storage in RAM in ROM/RAM 226 under control of DMA 228. Microprocessor 224 may employ digital signal analysis techniques to characterize the digitized signals stored in ROM/RAM 226 to recognize and classify the patient's heart rhythm employing any of the numerous signal processing methodologies known to the art.

The PCD IPG circuitry of FIG. 2 provides atrial and/or ventricular cardiac pacing for bradycardia and tachycardia conditions and synchronized cardioversion and defibrillation shock therapies for tachyarrhythmias in accordance with therapy regimes programmed by the physician. With respect to the pacing operations, the pacer timing and control (PTC) circuitry 212 includes programmable digital counters which control the basic time intervals associated with bradycardia pacing modes including DDD, VVI, DVI, VDD, AAI, DDI and other modes of single and dual chamber pacing well known to the art. PTC circuitry 212 also controls escape intervals associated with timing and delivering anti-tachyarrhythmia pacing in both the atrium and the ventricle, employing any anti-tachyarrhythmia pacing therapies known to the art. In the process, PTC circuitry 212 also times the operation of and processes A-SENSE and V-SENSE events of the atrial and ventricular sense amplifiers 204 and 200.

In normal pacing modes of operation, intervals defined by PTC circuitry 212 include atrial and ventricular pacing escape intervals, blanking intervals, the refractory periods during which sensed P-waves and R-waves are ineffective to restart timing of the escape intervals, and the pulse widths of the pacing pulses. These intervals are determined by microprocessor 224, in response to stored data in RAM in ROM/RAM 226 and are communicated to the PTC circuitry 212 via address/data bus 218. PTC circuitry 212 also determines the amplitude of the cardiac pacing pulses under control of microprocessor 224.

During bradycardia pacing, the escape interval counters within PTC circuitry 212 are reset upon sensing of R-waves and P-waves as indicated by a signals on lines 202 and 206. In accordance with the selected pacing mode, PTC circuitry 212 triggers generation of atrial and/or ventricular pacing pulses by APACE and VPACE output circuits 214 and 216 on time-out of the appropriate escape interval counters. The pacing escape interval counters are also reset on generation of pacing pulses, and thereby control the basic timing of cardiac pacing functions.

Isolation circuits 203 and 201 operate to disconnect the input terminals of atrial and ventricular sense amplifiers 204 and 200 from the APACE and VPACE output circuits 214 and 216 on time-out of the atrial and ventricular escape intervals for a short time under the control of the PTC circuitry 212 in a manner well known in the art. Blanking of the atrial and ventricular sense amplifiers 204 and 200 is also provided by PTC circuitry 212 in accordance with the conventional practice. Although not shown in FIG. 2, it will be understood that high voltage protection power FETs are incorporated within switch matrix and protection circuit 208 between the atrial and ventricular pace/sense terminals, 160, 162 and 164, 166 and the APACE and VPACE output circuits 214 and 216, respectively, to protect against IC damage from cardioversion/defibrillation shock energy induced across the electrodes of the pace/sense leads when such shocks are delivered.

With respect to anti-tachyarrhythmia pacing, the value of the counts present in the escape interval counters when reset by sensed R-waves and P-waves may be used as measures of the durations of R-R intervals, P-P intervals, P-R intervals and R-P intervals, which measurements are stored in RAM in ROM/RAM 226 and used to detect the presence of tachyarrhythmias as described below. Microprocessor 224 operates as an interrupt driven device, and is responsive to interrupts from PTC circuitry 212 corresponding to the occurrence sensed P-waves (P-OUT) and R-waves (R-OUT) and corresponding to the generation of cardiac pacing pulses. These interrupts are provided via data/address bus 218. Any necessary mathematical calculations to be performed by microprocessor 224 and any updating of the values or intervals controlled by PTC circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P interval) may be stored. Preferably, a portion of RAM in the ROM/RAM 226 (FIG. 2) is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. Appropriate ventricular tachyarrhythmia detection methodologies measuring such factors are described in the article "Onset and Stability for Ventricular Tachyarrhythmia Detection in an Implantable Pacer-Cardioverter-Defibrillator" by Olson et al., published in *Computers in Cardiology*, Oct. 7-10, 1986, IEEE Computer Society Press, pages 167-170, incorporated herein in its entirety. Appropriate atrial tachycardia, fibrillation and flutter detection methodologies are disclosed in the article "Automatic Tachycardia Recognition", by Arzbaecher et al., published in *PACE*, Vol. 7, May-June 1984, part II, pages 541-547 and in PCT Application No. US 92/02829, Publication No. WO 92/18198 by Adams et al., both incorporated herein by reference in their entireties. In the PCT application, careful synchronization of the high voltage atrial defibrillation shock to the ventricles to avoid induction of ventricular tachycardia or fibrillation is also discussed.

In the event that an atrial or ventricular tachyarrhythmia is detected, and an anti-tachyarrhythmia pacing regimen is prescribed, appropriate timing intervals for controlling generation of anti-tachyarrhythmia pacing therapies are loaded from microprocessor 224 into the PTC circuitry 212, to control the operation of the escape interval counters therein and to define refractory periods during which detection of R-waves and P-waves is ineffective to restart the escape interval counters.

In the event that generation of a cardioversion or defibrillation shock is required, microprocessor 224 employs the an escape interval counter to control timing of such cardioversion and defibrillation shocks, as well as associated refractory periods. In response to the detection of atrial or ventricular fibrillation or tachyarrhythmia requiring a cardioversion shock, microprocessor 224 activates cardioversion/defibrillation control circuitry 230, which initiates charging of the high voltage capacitors 246 and 248 via charging circuit 236, under control of high voltage charging control line 240. The voltage on the high voltage capacitors 246–249 is monitored via VCAP line 244, which is passed through multiplexer 220. In response to reaching a predetermined value set by microprocessor 224, the voltage on VCAP line 244 results in generation of a logic signal on Cap Full (CF) line 254, terminating charging. Thereafter, timing of the delivery of the defibrillation or cardioversion shock is controlled by PTC circuitry 212. Following delivery of the shock therapy, the microprocessor 224 then returns the operating mode to cardiac pacing and awaits the next successive interrupt due to pacing or the occurrence of a sensed atrial or ventricular depolarization.

In the illustrated operating system, delivery of the cardioversion or defibrillation shocks is accomplished by output circuit 234, under control of control circuitry 230 via control bus 238. Output circuit 234 determines whether a monophasic or biphasic shock is delivered, the polarity of the electrodes and which electrodes are involved in delivery of the shock. Output circuit 234 also includes high voltage switches which control whether electrodes are coupled together during delivery of the shock. Alternatively, electrodes intended to be coupled together during the shock may simply be permanently coupled to one another, either exterior to or interior of the device housing, and polarity may similarly be pre-set, as in current implantable defibrillators. An example of output circuitry for delivery of biphasic shock regimens to multiple electrode systems may be found in U.S. Pat. No. 4,727,877, incorporated by reference in its entirety.

In modern implantable PCD IPGs, the particular therapies are programmed in during a patient work up by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On re-detection of tachycardia, a more aggressive anti-tachycardia pacing therapy may be scheduled. If repeated attempts at anti-tachycardia pacing therapies fail, a higher level cardioversion shock may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion shocks if the rate of the detected tachycardia is above a preset threshold. The references cited above in conjunction with descriptions of prior art tachycardia detection and treatment therapies are applicable here as well.

In the event that atrial or ventricular fibrillation is identified, the typical therapy will be delivery of a high amplitude defibrillation shock, typically in excess of 10.0 joules in the case of ventricular fibrillation and about 5.0 joules or less in the case of atrial defibrillation. Lower energy levels will be employed for cardioversion. As in the case of currently available implantable pacemakers/cardioverter/defibrillators, and as discussed in the above-cited references, it is envisioned that the amplitude of the defibrillation shock may be incremented in response to failure of an initial shock or shocks to terminate fibrillation.

The criteria for detection of a tachyarrhythmia and the particular selection of the cardioversion/defibrillation terminals and associated cardioversion/defibrillation electrodes for delivery of the physician prescribed therapies are not of primary importance in the practice of the present invention. The method of the present invention, however, is only practiced when the HV charge circuit 236 is not being operated in response to a detected tachyarrhythmia and when cardioversion/defibrillation therapies are not being delivered.

Turning to the lead integrity test operations of the present invention, a lead impedance measurement logical interface (LIMLI) 260 is provided and employed in a test mode initiated by commands from the microprocessor 224 on address/data bus 218 either automatically on a periodic basis or in response to a programmed-in command received through telemetry. Very generally, when the lead impedance test mode is initiated by microprocessor 224, a "force" terminal pair and a "measure" terminal pair having only the lead under test in common are selected from among defibrillation terminals 170, 172 and 174/110 and pace/sense terminals 160, 162 and 164, 166 (through connections made in switch matrix and protection circuit 208 and output circuit 234 as described below). In the following description, the term "lead" comprises a single electrode and lead conductor having a proximal connector element for connection to one of these terminals, even though it may be part of a bipolar or tripolar pacing or cardioversion/defibrillation lead as described above, and includes the CAN electrode 110 and associated electrical connections between it an terminal 174. The "lead impedance" as further defined below includes the intrinsic lead resistive impedance that may be measured between the distal electrode and the proximal connector element when the lead is not implanted. This intrinsic lead impedance is a relatively low value for a lead without any insulation defects or loose or open internal connections with the proximal connector element and the distal electrode. The lead impedance that is actually measured when the lead is implanted includes the electrode/tissue interface impedance (ETI), and also includes any impedance caused by a loose or otherwise poor electrical connection of the proximal lead connector element with the IPG connector block connector element. The ETI impedance may be considered a resistive impedance, for purposes of the lead integrity test and varies depending on electrode surface area/shape and associated current density. The total normal lead impedance value ranges for any particular lead design and combinations of excitation and measure lead pairs may be derived empirically from clinical experience gained over time.

A sub-threshold, excitation or "force", lead impedance voltage pulse (LIPULSE or $V_p$) of predetermined amplitude and pulse width is generated by a force pulse generator within LIMLI 260. The force pulse $V_p$ is applied to the terminal of the force terminal pair not coupled to the lead under test (the "driven terminal") while the terminal of the lead under test is held at system ground. The excitation path therefore is through the driven terminal, the lead not under test, the patient's body and/or heart tissue, the lead under test, and system ground. A measure path is also selected which includes a measure terminal different from the driven terminal, the lead coupled thereto, the patient's body and/or heart tissue, the lead under test and its terminal at system ground. It should be noted that the force pulse $V_p$ could be in the form of a current pulse instead of a voltage pulse, and, in either case, may consist of one or more phases of differing polarity. For simplicity, the force pulse $V_p$ is assumed to be a constant voltage pulse.

The electrical current delivered to the excitation path during the delivery of the force pulse $V_p$ is measured as a signal $I_m$ in the LIMLI 260. At the same time, the voltage appearing across the measure terminal pair is measured as the signal $V_m$ in LIMLI 260. The measure and force terminal pairs have the lead under test in common, and no current flows through the lead coupled to the measure terminal. From the measured current $I_m$ flowing into the excitation path and the measured voltage $V_m$ induced across the measure path between the measure terminal pair, it is possible to calculate the apparent impedance of the lead under test and infer the state of lead integrity by comparison to maximum and minimum impedance threshold values. If the calculated impedance is within the acceptable impedance range, the lead under test may be assumed to not have a lead integrity failure. However, since the excitation path and the measure path include the two other leads, a further diagnosis of the lead impedances obtained after concluding lead integrity tests of all of the involved leads may be necessary to determine which lead exhibits a lead integrity failure.

Very generally, in one approach illustrated in FIG. 2, the measured current $I_m$ and voltage $V_m$ are employed to derive a lead impedance in microprocessor 224 that is then employed by the microprocessor 224 in a diagnostic comparison to normal impedance values in order to diagnose tentative lead integrity failures. The impedance thresholds for the particular leads under test are derived in advance from characteristics of the lead type or model under test and stored in RAM/ROM 226 for use by the microcomputer 224. When a lead impedance failure is tentatively diagnosed from the comparison, a patient warning is invoked in patient warning device 242 to alert the patient to contact the attending medical personnel. A suitable patient perceptible, acoustic alarm that is employed in the SynchroMed™ implantable drug administration device marketed by the assignee of the present invention may be employed as patient warning device 242.

Whether or not a lead integrity failure is diagnosed by microcomputer 224, the impedance data may also be stored in RAM in ROM/RAM 226 until telemetry out is initiated. The impedance data may be collected on a regular schedule and be stored with related data for later telemetry out. The stored data may be compressed, for example as weekly high and low impedance values, and retained for extended periods of time. When telemetered to the external programmer, they may be displayed by the external programmer and interpreted by the physician with assistance of a programmer-resident lead impedance thresholds and an analysis program to display lead impedance trends and diagnose potential faulty lead insulation or lead conductor fractures involving all the potential lead integrity failure combinations of a unipolar, bipolar or tripolar lead.

Figure 3:
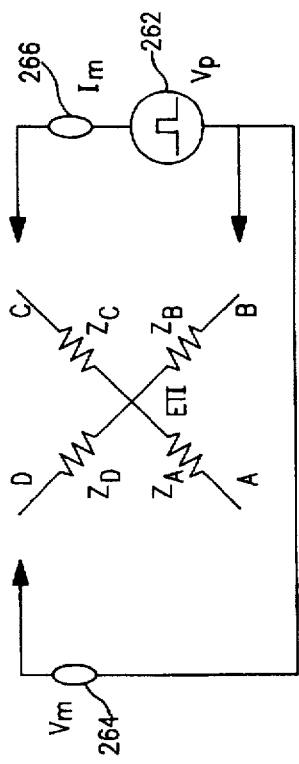
FIGS. 3 and 4 are simplified diagrams illustrating the manner in which integrity of a defibrillation lead and electrode is determined by the sequential deliveries of force pulses and the measurements of current and voltage through paths including the defibrillation lead and electrode subjected to the test.

To illustrate how the intrinsic and extrinsic lead and electrode impedance of a particular lead may be indirectly derived from measured currents and voltages without applying a test pulse directly to the lead under test, consider the illustration depicted in the diagram of FIG. 3 where there are four leads in the PCD system designated A, B, C, D. The leads A, B, C, D are deemed to be, and are illustrated as, electrically connected together through the contact of their respective electrodes with the intervening, conductive, heart and body tissue and fluids at the ETI to form the excitation and measurement paths between selected terminal pairs. Four impedances $Z_A$, $Z_B$, $Z_C$, $Z_D$ are associated with the lead impedance and the ETI of each respective lead A, B, C, D. The illustrated lead impedances also include any impedance caused by a loose or otherwise poor electrical connection of the proximal lead connector elements with the IPG connector block connector elements at the terminals illustrated in FIG. 2.

In this exemplary diagram of FIG. 3, leads A and B are assumed to represent a pair of high voltage defibrillation leads, whereas leads C and D are assumed to represent a pair of low voltage pacing leads. To avoid costly and bulky circuit protection in circuit with the high voltage defibrillation leads, it is desired to avoid coupling a test pulse generator for applying a force pulse $V_p$, (either positive or negative with respect to system ground), or a current or voltage measuring circuit directly to the terminals of high voltage defibrillation leads A and B. Therefore, the terminal of the high voltage cardioversion/defibrillation lead A or B under test is coupled to system ground, and the force pulse $V_p$ is applied to the terminal of a pacing lead C or D. Assume that lead B is the "lead under test", the excitation path is across lead C and lead B, the lead B terminal is at system ground and the force pulse $V_p$ is applied by a pulse generator 262 to the driven terminal of lead C, the "force lead" in this example. Also assume that the measure path is across lead D (the "measure lead") and lead B with the lead B terminal again at system ground (which is isolated from the ETI). A current monitoring instrument 266 is coupled in series with the driven terminal of force lead C and used to determine the current $I_m$ flowing through leads B and C. At the same time, the induced voltage $V_m$ is measured across the measure path, that is across the measure terminal of measure lead D and the grounded terminal of the lead B under test (alternatively, lead A could be used instead of lead D) by a voltage measuring instrument 264. Absent any other current source, it is also safely assumed that there is no appreciable current flowing through the measure lead D, the unused lead A or the voltage measuring instrument 264. The ratio of the induced voltage $V_m$ to the force current $I_m$ will results in a value assumed to be the effective lead impedance $Z_B$ of lead B.

If the measured value of the impedance $Z_B$ falls outside of a specified impedance range, a failure of the lead B continuity can be implied. For example, if the impedance $Z_B$ is below the lower range of allowable impedances, it could be implied that there is an inter-electrode insulation failure between components of leads B and D or leads B and A. On the other hand, if the impedance $Z_B$ is above the upper range of allowable impedances, it can be implied that there is a lead integrity problem (i.e., an open circuit) along the length of the lead D conductor or the lead A conductor or the length of the typically spiral wound, exposed defibrillation electrode, or at a connection of the electrode or the proximal connector terminal element with the lead B conductor, or in the connection of the lead connector element with the IPG terminal. Alternatively, the high impedance could be due to a degradation of the ETI, e.g., a substantial loss of contact of the electrode surface with the heart or body tissue. Either sudden significant changes and/or long-term drift (i.e., impedance trend changes) in the measured impedance could be indicators of lead/electrode integrity problems.

Figure 4:
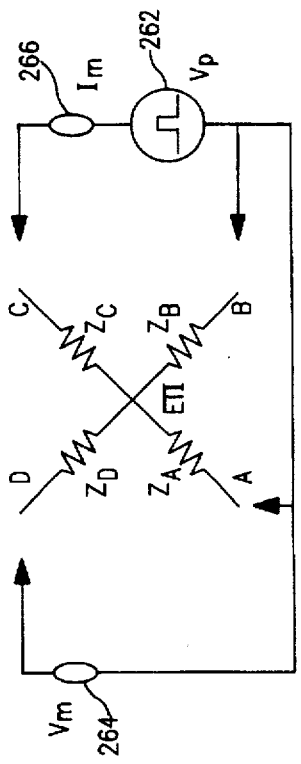

Repeating this lead integrity test for all combinations of the four leads A, B, C, D, results in derivation of all four lead impedances $Z_A$, $Z_B$, $Z_C$, $Z_D$ for the four leads under test. For example, consider the situation where, after having determined the impedance $Z_B$, the force pulse $V_p$ is delivered between leads C and A, and the induced voltage $V_m$ is measured between leads D and A as illustrated in FIG. 4. Assuming that there is no current flow through either lead B or the voltage measuring instrument 264, the ratio of the measured voltage $V_m$ to measured current $I_m$ provides the lead impedance represented by $Z_A$. Not only is it possible as above to make conclusions regarding lead A integrity, but it is also possible to infer the impedance between leads A and B from the sum of the results of the individual measurements of $Z_A$ and $Z_B$. This inference can also be used to make implications regarding lead integrity of leads A and B.

Theoretically, the measurements of the pacing lead impedances $Z_C$ and $Z_D$ may be derived in the same manner, and the process may be repeated for five or more leads in the system to derive a complete set of lead impedances $Z_A$, $Z_B$, . . . $Z_N$. However, in practice, the pacing lead terminals may already be protected by cardioversion/defibrillation energy protection devices, and their impedances may be derived in the conventional manner as shown in the following preferred embodiment.

Another method to assess the lead integrity between leads A and B involves configuring the force pulse generator 262 and the induced voltage measuring instrument 264 such that it is possible to measure the impedance combinations $Z_B+Z_C$ (force and measure between leads B and C), $Z_A+Z_C$ (force and measure between leads A and C), and $Z_C$ in series with the parallel combination of $Z_A$ and $Z_B$ (short leads A and B together and force and measure between that point and lead C). This results in a set of three equations and three unknowns which can be solved for impedances $Z_A$ and $Z_B$.

Returning to the illustrated PCD system of FIG. 1 and IPG block diagram of FIG. 2, the principles illustrated in FIGS. 3 and 4 can advantageously be implemented in a preferred embodiment using a sub-set of the RV COIL, RA-SVC COIL and CAN leads/electrodes, e.g. the RV COIL and CAN electrodes, in conjunction with atrial and ventricular pacing leads/electrodes. It is believed that the present invention is most readily practiced in the context of an IPG architecture having at least two cardioversion/defibrillation leads/electrodes, and that the present invention can therefore readily be practiced using the basic hardware of existing microprocessor controlled, single chamber PCD systems, or in proposed dual chamber PCD systems of the types listed above. The invention may be implemented primarily by means of variations in the software stored in the ROM/RAM 226, switch matrix 208 and PTC circuitry 212, LIMLI 260 and a further force pulse generator for the particular combinations of atrial and/or ventricular sense/pace and cardioversion/defibrillation functions in the particular PCD device configuration.

Figure 5:
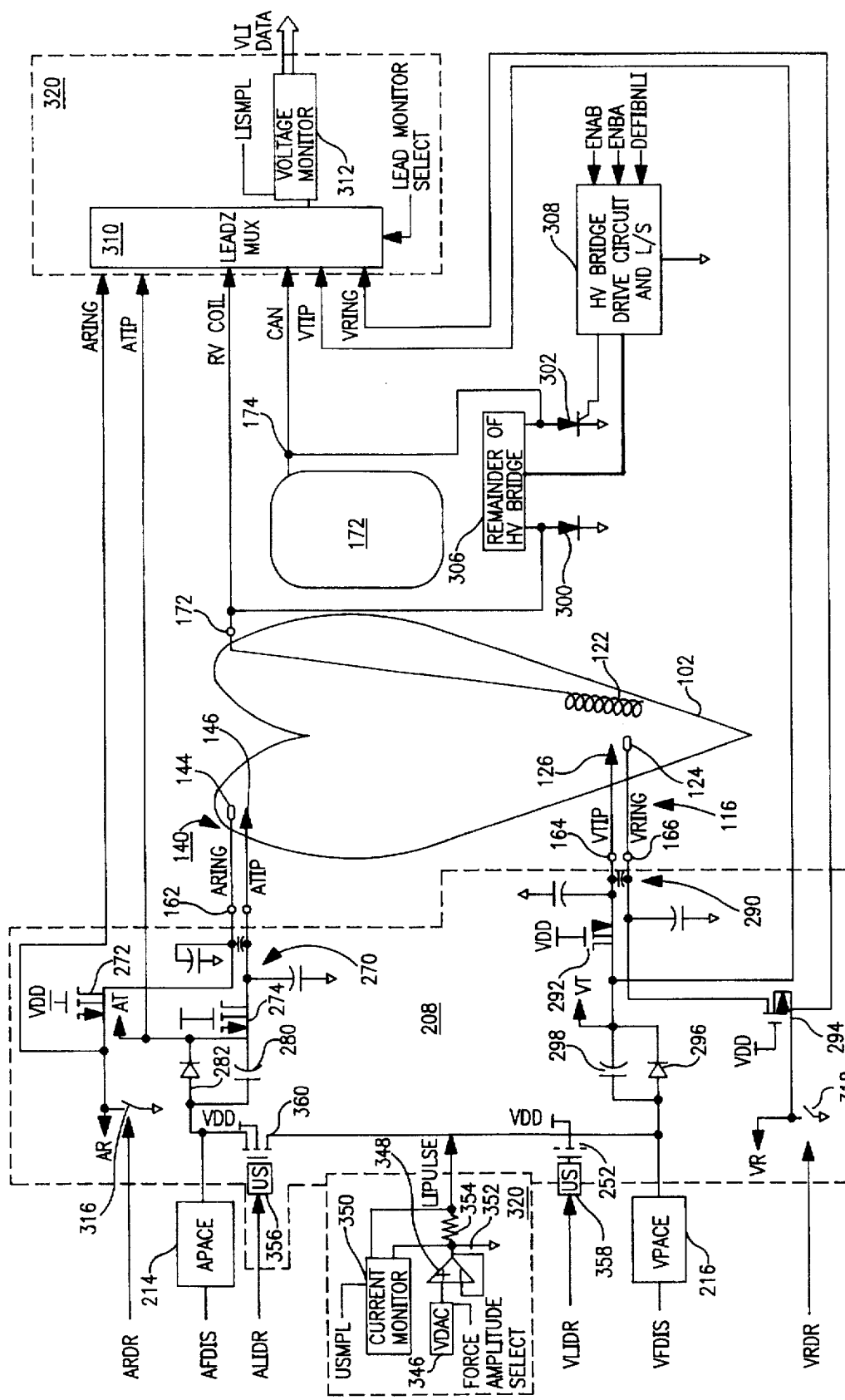
FIG. 5 is a schematic illustration of the electrode interface for lead impedance measurement incorporated into a specific example of a PCD system of FIGS. 1 and 2 in accordance with a preferred embodiment of the invention.
Figure 6:
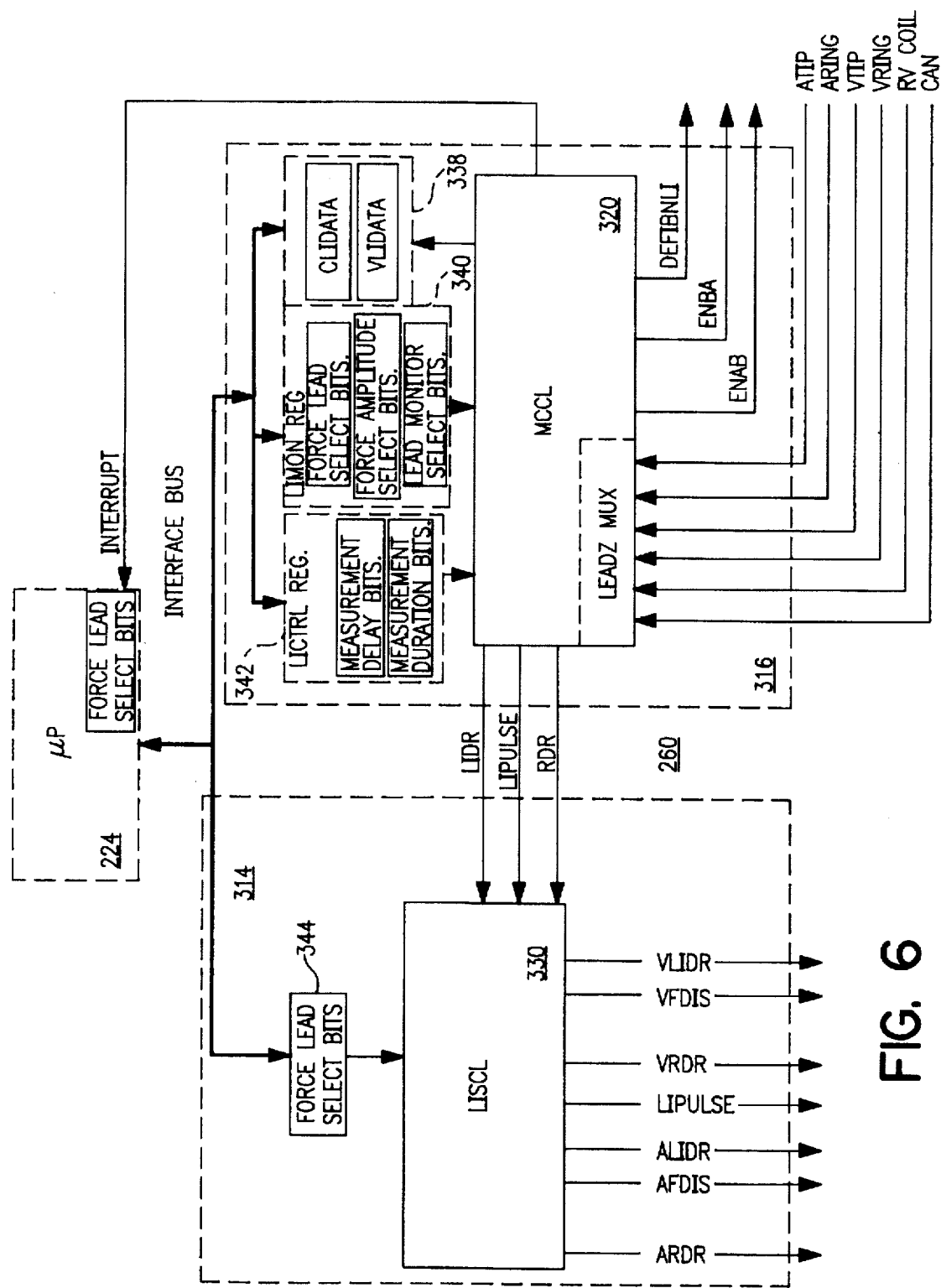
FIG. 6 is a schematic illustration of the logical interface for lead impedance measurement incorporated into the specific example of the PCD system of FIGS. 1 and 2 illustrated in FIG. 5 in accordance with the preferred embodiment of the invention.

FIGS. 5 and 6 further depict the components of LIMLI 260 in relation to one such embodiment of a PCD system in which the invention may be practiced employing atrial and ventricular pacing and sensing functions and ventricular cardioversion/defibrillation functions. As shown in FIG. 5, the atrial lead 140 includes atrial ring (ARING) and distal tip (ATIP) electrodes 144 and 146 and associated conductors coupled to terminals 160 and 162 but does not include an atrial cardioversion/defibrillation electrode and related components of the comprehensive embodiment of FIG. 1 The ventricular lead 116 includes ventricular ring (VRING) and distal tip (VTIP) electrodes 124 and 126 and associated lead conductors coupled to terminals 164 and 166. The RV COIL electrode 122 may be formed as part of the ventricular lead 116 as described above in reference to FIG. 1, and its associated lead conductor is coupled to terminal 172. The IPG CAN electrode 110 is used in this example with the RV COIL electrode 122 for delivery of cardioversion/defibrillation shocks to the ventricle of heart 102 through terminal 174.

The atrial and ventricular leads 140 and 116 are also depicted in FIG. 5 in relation to the APACE and VPACE output circuits 214 and 216 and associated components of switch matrix and protection circuit 208 for protection of the pacing and sensing circuits from high voltage cardioversion/defibrillation shocks. In this regard, the atrial and ventricular sense input lines AR, AT and VR, VT extend from the illustrated components of switch matrix and protection circuit 208 to the isolation circuits 201 and 203 of FIG. 1, respectively.

Within the switch matrix and protection circuit 208, and with respect to the atrial lead 140, the ARING and ATIP lead conductors are capacitively coupled to one another and to ground through capacitor set 270. Normally conductive, atrial high voltage protection FETs 272 and 274 are coupled to VDD and in series with the ARING and ATIP lead conductors. The high voltages and currents induced in the ARING and ATIP lead conductors during delivery of a cardioversion/defibrillation shock reverse bias and turn off FETs 272 and 274 thereby protecting the atrial sense amplifier 204 and APACE output circuit 214. A recharge current coupling capacitor 280 and diode 282 are connected between the APACE pulse generator 214 and the ATIP conductor for regulating recharge current following delivery of an APACE pulse to dissipate electrical after-potentials or polarization at the ATIP electrode in a manner well known in the art.

Similarly, the VTIP and VRING electrical conductors are capacitively coupled to one another and to ground through capacitor set 284, and normally conductive, ventricular high voltage protection FETs 292 and 294 are coupled in series with the VRING and VTIP lead conductors for cardioversion/defibrillation shock energy protection in the same manner. A recharge current coupling capacitor 298 and diode 296 are connected between the VPACE pulse generator 216 and the VTIP conductor for regulating recharge current following delivery of an VPACE pulse.

The ATIP and VTIP lead conductors and electrodes are normally coupled to the outputs of the APACE and VPACE output circuits 214 and 216, respectively, through the parallel diode and capacitor circuits and through AT and VT terminals to inputs of the atrial and ventricular isolation circuits 203 and 201, respectively, as shown in FIG. 2. The ARING and VRING lead conductors and electrodes are normally coupled at AR and VR terminals to the other inputs of the atrial and ventricular isolation circuits 203 and 201, respectively, in the programmed PCD operating modes. The isolation FETs 272, 274 and 292, 294 protect the isolation circuits 203 and 201 and the APACE and VPACE output circuits 214 and 216.

FIG. 5 also shows portions of the high voltage output circuit 234 in relation to signals received from the LIMLI illustrated in FIG. 6. During a lead integrity determination in accordance with the present invention, the CV/DEFIB control circuit 230 of FIG. 2 is disabled by a command from microcomputer 224. In addition, a back-up disabling signal (DEFIBNLI) generated by monitoring/conversion circuits and control logic (MCCL) 320 shown in FIG. 6 is applied to the HV bridge drive circuit and level shifter (L/S) 308 of the output circuit 234. It is also necessary to couple the defibrillation/cardioversion lead/electrode under test to system ground. Part of the bridge circuit in high voltage output circuit 234, specifically the HV SCR's 300 and 302, block 306 and the HV bridge drive circuit and L/S 308 are employed to ground the terminal of the selected RV COIL electrode 122 or CAN electrode 110 during the test. In this regard, the HV SCR 300 or 302 is rendered conductive by a high voltage drive signal generated by the HV bridge drive circuitry 308 to ground the RV COIL electrode 122 or the CAN electrode 110, respectively, in response to applied ENAB or ENBA signals generated by MCCL 320 as described below.

Each of the ARING, ATIP, VRING, VTIP, and RV COIL leads/electrodes and the CAN electrode 110 are electrically connected to input terminals of a lead impedance multiplexer 310 forming part of MCCL 320. A lead monitor select signal from a lead monitor select register illustrated in FIG. 6 is applied to select the particular combination of lead conductors or CAN 110 for the particular test. The voltage monitor 312 is then enabled by a lead impedance sampling (LISMPL) signal also generated within the LIMLI illustrated in FIG. 6 and described below to measure the induced voltage across the selected electrode pair, digitize it and store it in a voltage lead impedance data (VLIDATA)

register in a conversion results register 338 as described further below in reference to FIG. 6. Following each lead integrity test in the lead integrity test mode, the APACE and VPACE pulse generators 214 and 216 are also triggered by AFDIS and VFDIS signals generated by the lead impedance sampling/interface control logic (LISCL) circuit 330 of FIG. 6 to discharge any residual charge on the capacitors 280 and 298, respectively, of the driven terminal pair.

When a lead integrity test is initiated involving the ring electrodes, the ARING drive (ARDR) or VRING drive (VRDR) signals are selectively generated by the LISCL 330 to close normally open switches 316 or 318 to ground the ARING or VRING conductor and electrode, respectively. The particular switches closed depends on the combination of leads selected by the microprocessor 224 at a particular stage in the lead integrity test operation. In this illustrated embodiment, the ATIP, ARING and VRING lead/electrodes are not employed in deriving the RV COIL and CAN impedances.

When a lead integrity test is initiated using the ATIP or VTIP lead as the force lead, the atrial or ventricular lead impedance drive (ALIDR) or (VLIDR) signals are selectively generated by the LISCL 330 in response to the LIDR signal from MCCL 320 and the identified force lead select bit. The ALIDR or the VLIDR signal is applied through level shifter 356 or 358 to close normally open switch 360 or 362, respectively, to allow the LIPULSE to be applied to the terminal 160 or 164 to which the ATIP or VTIP lead/electrode is attached. As described in reference to FIG. 6, the LIPULSE is generated in the MCCL 320 and applied through the LISCL 330 to the FETs 360 and 362. In accordance with this preferred embodiment of the invention, the terminals 160 and 164 coupled to the ATIP and VTIP leads/electrodes are used as the non-grounded drive terminals of the excitation paths for the lead integrity tests of the CAN and RV COIL leads/electrodes. The terminal of the remaining selected one of the ARING, VRING, CAN or RV COIL lead/electrode of each drive terminal pair is set to system ground by the ARDR, VRDR, ENBA or ENAB signal. Alternatively, the ARING and VRING electrodes could be used as the non-grounded drive terminals of the exitation pathsforthe CAN and RV COIL electrodes.

Referring to both FIGS. 5 and 6, the lead integrity test sequence is initiated by microprocessor 224 at a specified time each day or other interval or upon receipt of a programmed-in command. As described above, the test cannot be initiated if an anti-arrhythmic therapy regimen is in progress. In order to avoid any interference with pacing operations, the lead integrity test is timed to occur within a measurement duration of 61 micro-seconds, for example, after a measurement delay from a preceding paced or sensed event that is preferably set at 59 mS, for example.

Turning to the selection of the drive terminal pair and in reference to FIG. 6, the programmable measurement duration and measurement delay are retrieved from bits of a lead impedance control (LICTRL) register 342 by the MCCL 320 and are used to generate the LIDR pulse and the RDR pulse applied to the LISCL 330 at appropriate times. The force lead select bits are written from a register in microprocessor 224 to the force lead select bits 344 of a register in force block 314 and into the force lead select bits of LIMON register 340. When the force lead select bits identify the lead under test to be a pacing lead, the LISCL 330 responds to the lead select bits and the LIDR and RDR signals to generate the appropriate drive and measure terminal pair drive signals ALIDR, VLIDR, ARDR, or VRDR to close the switches 356, 358, 316 or 318, respectively. When the force lead select bits in the LIMON register identifies the lead under test to be the RV COIL lead or CAN electrode, the MCCL 320 generates VLIDR signal to close switch 358, the appropriate ENAB or ENBA signal to couple the terminal 172 or 174 to ground, and the DEFIBNLI signal to disable the delivery of a cardioversion/defibrillation shock as described above. The timing of the generation of the ENBA, ENAB and DEFIBNLI signals is determined by MCCL 320 from the measurement delay and measurement duration bits in LICTRL register 342.

Referring back to FIG. 5, the force amplitude select bit is read out of the LIMON register and converted by the voltage digital-to-analog converter (VDAC) 346 to an analog voltage applied to one input terminal of op amp 348 in MCCL 320. The output of op amp 348 is applied across capacitor 352 and to resistor 354 generating the force pulse or LIPULSE at a time preceding the generation of the appropriate pair of drive terminal pair signals ALIDR, VLIDR, ARDR, VRDR, ENBA or ENAB. The LIPULSE is applied (through LISCL in FIG. 6) to the driven terminal 160 or 164 through the FET switch 360 or 362 of the switch matrix and protection circuit 208 that is closed by the appropriate applied ALIDR or VLIDR signal from LISCL 330. In this preferred embodiment, the driven terminal to which the LIPULSE is applied is always either the ATIP or VTIP electrode, and the grounded terminals of the driven pair are always the ARING, VRING, CAN or RV COIL terminals.

The selected measure terminal pair for measuring the induced voltage $V_m$ is determined by the MCCL 320 from the lead monitor select bits of LIMON register 340. The measure terminal pair includes a lead other than the force lead and the lead under test. The terminal of the lead under test remains coupled to system ground by the appropriate ENAB, ENBA, ARDR or VRDR signal. The lead monitor select bits from the LIMON register are used by MCCL 320 to switch the identified measure terminal pair through the multiplexer 310 to the input terminals of voltage monitor 312. The LISMPL signal is generated within MCCL 320 to enable voltage monitor 312 for a short interval prior to the delivery of the LIPULSE to measure any baseline $V_m$ of the voltage monitor 312 while coupled via multiplexer 310 with the selected measure terminal pair. After the baseline measurement delay times out, the LISMPL signal continues to be applied to the voltage monitor 312 to enable $V_m$ measurement of the voltage applied to the lead under test. At the same time, the LISMPL signal is applied to the current monitor 350 in MCCL 350 to measure the delivered current $I_m$.

The resulting measured $V_m$ and $I_m$ analog values are digitized in MCCL 320. The digitized $V_m$ and $I_m$ values are logarithmically encoded in MCCL 320 and stored as VLIDATA and CLIDATA, respectively, in the respective conversion results registers 338. When these operations are completed for the prescribed force lead select bits and lead monitor select bits, an interrupt from the MCCL 320 signals the microprocessor 224 that the VLIDATA and CLIDATA is stored. A logarithmic impedance value is derived by microprocessor 224 by subtracting the CLIDATA value from the VLIDATA value. The next lead integrity test is commenced after an intervening paced or sensed event and the attendant delays. The microprocessor 224 commences the next lead integrity test by writing new force lead select bits, force amplitude select bits, and lead monitor bits in LIMON register 340 and may change the measurement delay bits and measurement duration bits in LICTRL register 342 depending on the combination. When all prescribed lead integrity tests are completed, the lead integrity test mode is exited.

Lead integrity tests are accompanied by the comparisons of the CLIDATA value against tolerances. If the $I_m$ is outside upper and lower limits, the stored impedance results are associated with an invalid, out of specification current value, flag. In addition, the impedance values are compared to upper and lower impedance limits, and the patient alarm is commenced in order to warn the patient to contact his/her physician to determine if a serious problem is present. The impedance values are stored in ROM/RAM registers with associated data as described above for telemetering out in an interrogation initiated by the physician using an external programmer. The process is repeated for each force and measure combination until all of the prescribed lead integrity tests are made in the test mode. In the test mode, the lead integrity tests for each terminal combination are all made timed from a pace or sense event, and all six measurements are made in response to any request for a lead impedance measurement.

In one preferred embodiment, all of the daily impedance values are stored for a number of days, and if the registers are not cleared by the attending physician in a physician initiated interrogation, then the data is compressed into high and low readings thereafter and accumulated for a relatively long period, e.g. years, in the ROM/RAM registers.

Figure 7:
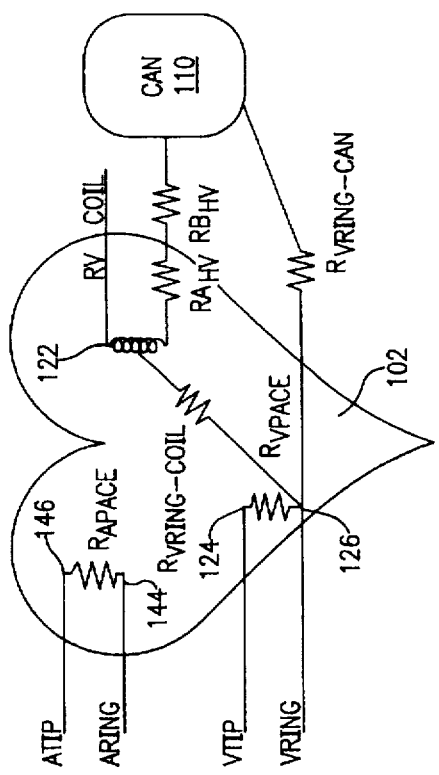
FIG. 7 is a simplified illustration of lead impedance values measured between the electrode example illustrated in FIGS. 5 and 6.

In the example of FIGS. 5 and 6, there are five leads/electrodes positioned in relation to the heart 102 and a sixth, remote CAN electrode 110, as also shown in FIG. 7 in relation to measured impedance values. The LIPULSE is forced between a force terminal pair coupled to a pair of Force Pulse Leads listed below in Table I while the excitation current $I_m$ flowing through the Force Pulse Leads is measured. The voltage $V_m$ is measured between a measure terminal pair coupled to a pair of Measure Leads selected by the microprocessor 224 operating through the force block 314 and the monitoring/conversion block 316. The "Leads" in this instance are defined as defined above with respect to FIGS. 3 and 4. The impedances to be monitored in this example are illustrated in FIG. 7 and listed in Table I as follows:

TABLE I

| Force Pulse Leads | Measure Leads | Impedance Values |
|---|---|---|
| VTIP to CAN | RV COIL to CAN | $RA_{HV}$ |
| VTIP to CAN | VRING to CAN | $R_{VRing-Can}$ |
| VTIP to COIL | CAN to RV COIL | $RB_{HV}$ |
| VTIP to COIL | VRING to RV COIL | $R_{VRing-Coil}$ |
| VTIP to VRING | VTIP to VRING | $R_{VPace}$ |
| ATIP to ARING | ATIP to ARING | $R_{APace}$ |

Two high voltage, RV COIL and CAN impedance measurements are made that result in the impedance values $RA_{HV}$ and $RB_{HV}$ listed above and shown in FIG. 7. The total lead impedance between the RV COIL lead and the CAN electrode is therefore the sum of the impedance values $RA_{HV}$ and $RB_{HV}$. In this manner, the total impedance $RA_{HV}+RB_{HV}$ can be obtained without directly driving an excitation voltage and measuring current the voltage and current between the electrodes.

In a PCD system having an atrial cardioversion/defibrillation capability using an RA-SVC COIL and/or a CS lead, similar measurements may be made using the ATIP lead as the force lead, particularly if the atrial lead body includes the RA/SVC COIL or CS lead. When lead integrity of the pace/sense leads are tested, the force pulse and monitor electrode/terminal pairs can be the same as shown in Table I because both are already protected by power FETs.

In the illustrated preferred embodiment of FIGS. 5–7, where a single ventricular lead body includes the VTIP, VRING and COIL electrodes and associated conductors and proximal connector elements, the VTIP and VRING are used to determine integrity failures as shown below in Table II. When an integrity failure constitutes an "open" somewhere in the measure path comprising the lead under test and the associated measure lead, a very low or zero CLIDATA current value is decoded and stored. An "invalid" current flag may be generated by the microprocessor in lieu of an impedance value which would be infinite or excessively high. At times, a "near open" condition may exist that is not reflected by a low enough current value $I_m$ to trigger the invalid current flag but does result in a lead impedance determination that exceeds a maximum lead impedance. After the impedance values and any invalid current flags are accumulated for all five lead/electrodes of FIGS. 6 and 7, the lead/electrode integrity may be determined from a set of rules set forth in the following Table II that take this consideration into account:

TABLE II

IMPEDANCE RULES

| FAILURE MODE | RULES<br>I = invalid or low current<br>OK = within tolerance<br>> Max = > Max Tolerance<br>< Min = < Min Tolerance | |
|---|---|---|
| COIL OPEN | $R_{VPace}$ = OK | & |
| | $RB_{HV}$ = I OR > Max | & |
| | $R_{Ring-Coil}$ > Max | & |
| | $R_{Ring-Can}$ = OK | |
| VRING OPEN | $R_{VPace}$ = I OR > Max | & |
| | $RA_{HV}$ = OK | & |
| | $RB_{HV}$ = OK | |
| VTIP OPEN | $R_{VPace}$ > Max | & |
| | $RA_{HV}$ = I OR > Max | & |
| | $RB_{HV}$ = I OR > Max | & |
| | $R_{Ring-Coil}$ = I OR > Max | & |
| | $R_{Ring-Can}$ = I OR > Max | |
| CAN OPEN | $R_{VPace}$ = OK | & |
| | $RA_{HV}$ = I OR > Max | & |
| | $R_{Ring-Coil}$ = OK | & |
| | $R_{Ring-Can}$ = I OR > Max | |
| VTIP-RV COIL SHORT | $R_{VPace}$ = OK | & |
| | $RA_{HV}$ = OK | & |
| | $RB_{HV}$ < Min. | & |
| | $R_{Ring-Coil}$ < Min | & |
| | $R_{Ring-Can}$ = OK | |
| VRING-VTIP SHORT | $R_{VPace}$ < Min. | & |
| | $RA_{HV}$ = OK | & |
| | $RB_{HV}$ = OK | & |
| | $R_{Ring-Coil}$ = OK | & |
| | $R_{Ring-Can}$ = OK | |
| VTIP-CAN SHORT | $RA_{HV}$ < Min. | & |
| | $R_{Ring-Coil}$ = OK | & |
| | $R_{Ring-Can}$ < Min | |
| VRING-RV COIL SHORT | $RA_{HV}$ = OK | & |
| | $RB_{HV}$ = OK | & |
| | $R_{Ring-Coil}$ < Min. | & |
| | $R_{Ring-Can}$ = OK | |
| VRING-CAN SHORT | $RA_{HV}$ = OK | & |
| | $RB_{HV}$ = OK | & |
| | $R_{Ring-Coil}$ = OK | & |
| | $R_{Ring-Can}$ < Min | |
| VRING/RV COIL OPEN | $R_{VPace}$ = I OR Max | & |
| | $RB_{HV}$ = I OR Max | |
| VRING/RV COIL-TIP SHORT | $RV_{Pace}$ < Min | & |
| | $RA_{HV}$ = OK | & |
| | $RB_{HV}$ < Min | & |
| | $R_{Ring-Coil}$ < Min | & |
| | $R_{Ring-Can}$ = OK | |
| VRING/RV COIL-CAN SHORT | $RA_{HV}$ < Min | & |
| | $RB_{HV}$ < Min | & |

TABLE II-continued

IMPEDANCE RULES

| FAILURE MODE | RULES<br>I = invalid or low current<br>OK = within tolerance<br>> Max = > Max Tolerance<br>< Min = < Min Tolerance |
|---|---|
| ATIP-ARING SHORT | $R_{Ring-Coil}$ < Min &<br>$R_{Ring-Can}$ < Min<br>$R_{APace}$ < Min |
| VTIP-VRING SHORT | $R_{VPace}$ < Min |
| ATIP OPEN OR ARING OPEN | $R_{APace}$ > Max |

From these values, the integrity of all leads in the system may be diagnosed as described above. The full diagnosis may be conducted by the physician from the impedance values for all of the lead integrity tests telemetered out through use of the programmer. The diagnosis may be automated in whole or in part within software resident in the programmer. Moreover, it may be implemented within the PCD IPG to more accurately determine the cause of an invalid flag or an out of acceptable impedance range determination before generating a patient alert. Alternatively, in the simplest case, a single invalid flag or out of acceptable range impedance measurement may be used to alert the patient to visit the medical care provider to make the diagnosis of the cause.

The preferred embodiments of the present invention allow the lead impedance measurements of the high voltage cardioversion/defibrillation electrodes to be conducted without the need for expensive and bulky circuit protection for the current monitor and the voltage monitor and associated circuitry.

Although the system and method described above provides the impedance determination from the measured current and voltage values and storage of the resulting impedance values in memory and/or transmission of the impedance values to an external programmer for each lead under test, it will be understood that the measured current and voltage values could instead be stored and/or transmitted out for conversion to impedance values in the external programmer or elsewhere.

In addition, although the system and method of the present invention is implemented advantageously in an implantable PCD system, it will be understood that the teachings of the invention may be implemented in other implantable tissue stimulators including pacemakers and other ICDs.

Although the impedances of the pacing leads are derived by the direct method in the preferred embodiment described above, it will be understood that they may also be derived in the manner of the invention by switching the roles of the pacing leads and defibrillation leads and the associated control switches and signals. Moreover, any combination of three pacing and defibrillation leads may be used in the derivation of the lead impedance of each lead under test by appropriate substitutions of the remaining two leads in the successive injections of first and second impedance test pulses and measurements of the injected currents and induced voltages.

As noted above, the force pulse may alternatively be a constant current pulse, with suitable limitations placed on the maximum current to be applied to avoid capture of the heart, that is delivered to the drive terminal pair. In that case, the voltage and current measurements described above would be reversed, but the equivalent impedance results would be obtained.

Although a microcomputer architecture implementation of the preferred embodiments is depicted for a variety of atrial and ventricular PCD configurations, it will be understood that the present invention may also be usefully practiced in all such configurations by means of a full custom integrated circuit in each case. For example, state machine architectures in which a state counter serves to control an arithmetic logic unit to perform calculations according to a prescribed sequence of counter controlled steps may be employed in the practice of the present invention.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

What is claim is:

1. In a tissue stimulation system having a pulse generator coupled through at least three terminals to at least three leads each having an electrode in contact with body tissue at an electrode/tissue interface, a method of testing current and voltage lead integrity of at least one of the leads comprising the steps of:

(a) selecting one of said at least three leads as a lead under test, a force lead and a measure lead;

(b) coupling the terminal of the lead under test to a fixed potential;

(c) driving an excitation voltage pulse in an excitation path including the terminal of the selected force lead, the force lead electrode/tissue interface, the lead under test electrode/tissue interface and the lead under test;

(d) measuring the excitation current value of the excitation voltage pulse delivered in the excitation path through the lead under test; and (e) measuring an induced voltage in a measure path including the terminal of the selected measure lead, the measure lead electrode/tissue interface, the lead under test electrode/tissue interface and the lead under test to determine lead integrity of the lead under test.

2. The method of claim 1 further comprising the step of:

(f) determining the lead impedance of the lead under test from the measured excitation current value and the induced voltage value.

3. The method of claim 2 further comprising the step of:

(g) repeating step (a) and changing the selection of the lead under test, the force lead and the measure lead; and (h) repeating steps (b)–(f) using the selection made in step (g).

4. The method of claim 3 further comprising the step of:

(i) repeating steps (g) and (h) until all leads of the tissue stimulation system are tested.

5. The method of claim 4 further comprising the steps of:

(j) comparing the lead impedances derived in step (f) with threshold impedance values; and (k) determining lead integrity from the results of the comparisons made in step (j).

6. The method of claim 1 further comprising the step of:

(f) repeating step (a) and changing the selection of the lead under test, the force lead and the measure lead; and (g) repeating steps (b)–(e) using the selection made in step (f).

7. The method of claim 6 further comprising the step of:
   (h) repeating steps (f) and (g) until all leads of the tissue stimulation system are tested.

8. In a tissue stimulation system having a pulse generator coupled through at least three terminals to at least three leads each having an electrode adapted to be in contact with body tissue at an electrode/tissue interface, a system for testing current and voltage lead integrity of at least one of said leads comprising:
   means for selecting one of said at least three leads as a lead under test, a force lead and a measure lead;
   means for coupling the terminal of the lead under test to a fixed potential;
   means for driving an excitation voltage pulse in an excitation path including the terminal of the selected force lead, the force lead electrode/tissue interface, the lead under test electrode/tissue interface and the lead under test;
   means for measuring the excitation current value of the excitation voltage pulse delivered in the excitation path through the lead under test; and
   means for measuring an induced voltage in a measure path including the terminal of the selected measure lead, the measure lead electrode/tissue interface, the lead under test electrode/tissue interface and the lead under test.

9. The system of claim 8 further comprising:
   means for determining the lead impedance of the lead under test from the measured excitation current value and the induced voltage value.

10. The system of claim 9 further comprising;
    means for changing the selection of the lead under test, the force lead and the measure lead for measuring the impedance of two or more of the leads in the system.

11. In an implantable pacing and defibrillation system having a pacing and defibrillation pulse generator coupled through a pacing lead terminal to at least one pacing lead having a pacing electrode implanted at a pacing electrode/ tissue interface in relation to the patient's heart, coupled through a defibrillation lead terminal to a defibrillation lead having a defibrillation electrode implanted at a defibrillation electrode/tissue interface in relation to a patient's heart, and coupled through a further lead terminal to a further lead having an electrode implanted at a further electrode/tissue interface in relation to the patient's heart, a method of testing lead integrity of at least one of said pacing lead, defibrillation lead, or further lead comprising the steps of:
    selecting one of said pacing lead, said defibrillation lead and said further lead as a lead under test, a force lead and a measure lead;
    coupling the terminal of the lead under test to a ground potential;
    driving an excitation voltage pulse in an excitation path including the terminal of the selected force lead, the force lead electrode/tissue interface, the lead under test electrode/tissue interface and the lead under test;
    measuring the electrical current value of the excitation voltage pulse delivered in the excitation path through the lead under test;
    measuring an induced voltage in a measure path including the terminal of the selected measure lead, the measure lead electrode/tissue interface, the lead under test electrode/tissue interface and the lead under test; and
    determining lead integrity of the lead under test from the measured electrical current value and the measured electrical voltage value.

12. The method of claim 11 wherein said determining step further comprises the steps of:
    deriving the lead impedance of the lead under test from the measured excitation current value and the induced voltage value; and
    comparing the lead impedance to a reference impedance value;
    determining from the comparison if the derived lead impedance value falls within a normal or abnormal lead impedance range.

13. The method of claim 12 further comprising the step of:
    changing the selection of the lead under test, the force lead and the measure lead; and
    repeating the steps of the method using the changed selection.

14. The method of claim 13 wherein the selected lead under test is the defibrillator lead, the force lead is the pacing lead, and the measure lead is the further lead.

15. The method of claim 11 further comprising the step of:
    changing the selection of the lead under test, the force lead and the measure lead; and
    repeating the steps of the method using the changed selection.

16. In an implantable pacing and defibrillation system having a pacing and defibrillation pulse generator coupled trough pacing lead terminals to a pacing lead having a pacing electrode implanted at a pacing electrode/tissue interface, coupled through a first defibrillation terminal to a first defibrillation lead having a first defibrillation electrode implanted at a defibrillation electrode/tissue interface in contact with a heart chamber, and coupled through a second defibrillation terminal to a second defibrillation lead and electrode, a method of testing the lead integrity of said first defibrillation lead comprising the steps of:
    selecting said pacing lead as a force lead;
    selecting said second defibrillation lead as a measure lead;
    selecting said first defibrillation lead as a lead under test;
    coupling the first defibrillation lead terminal to a ground potential;
    driving a first excitation voltage pulse in a first excitation path including the terminal of the selected force lead, the force lead electrode/tissue interface, the first defibrillation lead electrode/tissue interface and the first defibrillation lead;
    measuring the electrical current value of the excitation voltage pulse delivered in the first excitation path through the first defibrillation lead;
    measuring an induced voltage in a first measure path including the terminal of the selected measure lead, the measure lead electrode/tissue interface, the first defibrillation lead electrode/tissue interface and the first defibrillation lead;
    deriving a first impedance value from the measured electrical current and voltage values;
    selecting said first defibrillation electrode as a measure lead;
    selecting said second defibrillation electrode as a lead under test;
    coupling said second defibrillation lead terminal to a ground potential;
    driving a second excitation voltage pulse in a second excitation path including the terminal of the selected force lead, the force lead electrode/tissue interface, the second defibrillation lead electrode/tissue interface and the second defibrillation lead;

measuring the electrical current value of the excitation voltage pulse delivered in the second excitation path through the second defibrillation lead;

measuring an induced voltage in a second measure path including the terminal of the selected measure lead, the measure lead electrode/tissue interface, the second defibrillation lead electrode/tissue interface and the second defibrillation lead;

deriving a second impedance value from the measured electrical current and voltage values; and determining lead impedance between the first defibrillation lead and the second defibrillation lead from the sum of the first and second derived impedance values.

17. The method of claim 16 further comprising the steps of:

comparing the determined lead impedance with threshold impedance values; and determining lead integrity from the results of the comparison.

18. A method implemented in a PCD IPG and operable in a lead impedance test mode for deriving defibrillation lead impedances in a defibrillation lead system having first and second defibrillation leads each having defibrillation electrodes positionable in relation to a patient's heart for providing a defibrillation shock pathway through the patient's heart and electrically connected to said PCD IPG and employing a pacing lead system having first and second pacing leads each having pace/sense electrodes positioned in relation to a patient's heart for providing a pace/sense pathway through the patient's heart and electrically connected to said PCD IPG, said method comprising the steps of:

driving a first lead impedance test pulse of known voltage having insufficient energy to capture the heart into a first force pathway including the first pacing lead, the patient's body tissue and the first defibrillation lead;

measuring the current in the first force pathway during the first lead impedance test pulse;

measuring a first induced voltage, induced in response to said first lead impedance test pulse, across a first sense pathway including one of said second defibrillation lead or said second pacing lead, the patient's body tissue, and said first defibrillation lead;

deriving a first defibrillation lead impedance value from said measured current and induced voltage;

driving a second lead impedance test pulse of known voltage having insufficient energy to capture the heart into a second force pathway including said second pacing lead, the patient's body tissue and said second defibrillation lead;

measuring the current in said second force pathway during the second lead impedance test pulse;

measuring a second induced voltage, induced in response to said first lead impedance test pulse, across a second sense pathway including the other one of said second defibrillation lead or said second pacing lead, the patient's body tissue, and said second defibrillation lead under test; and deriving a second defibrillation lead impedance value from said measured current and induced voltage.

19. The method of claim 18 further comprising the steps of:

comparing the derived first and second defibrillation lead impedances with threshold impedance values; and determining integrity of the first and second defibrillation lead impedances from the results of the comparison.

20. The method of claim 18 further comprising the step of:

summing the derived first and second defibrillation lead impedances to derive the impedance between the first and second defibrillation leads.

* * * * *